US010481087B2

(12) United States Patent
Gao et al.

(10) Patent No.: US 10,481,087 B2
(45) Date of Patent: *Nov. 19, 2019

(54) SIMULATED INTEGRATED COMPUTATIONAL ELEMENTS AND THEIR APPLICATIONS

(71) Applicant: Halliburton Energy Services, Inc., Houston, TX (US)

(72) Inventors: Li Gao, Katy, TX (US); David L. Perkins, The Woodlands, TX (US); Michael T. Pelletier, Houston, TX (US); Christopher Michael Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 533 days.

This patent is subject to a terminal disclaimer.

(21) Appl. No.: 14/904,601

(22) PCT Filed: Sep. 3, 2013

(86) PCT No.: PCT/US2013/057852
§ 371 (c)(1),
(2) Date: Jan. 12, 2016

(87) PCT Pub. No.: WO2015/034468
PCT Pub. Date: Mar. 12, 2015

(65) Prior Publication Data
US 2016/0178511 A1 Jun. 23, 2016

(51) Int. Cl.
*G01N 21/39* (2006.01)
*G01N 33/28* (2006.01)
(Continued)

(52) U.S. Cl.
CPC .......... *G01N 21/39* (2013.01); *G01N 21/314* (2013.01); *G01N 21/33* (2013.01);
(Continued)

(58) Field of Classification Search
CPC ...... G01N 21/39; G01N 21/31; G01N 21/314; G01N 21/33; G01N 21/3577
See application file for complete search history.

(56) References Cited

U.S. PATENT DOCUMENTS 5,104,621 A 4/1992 Pfost et al.
6,474,152 B1 * 11/2002 Mullins ................ G01N 21/359
166/250.01
(Continued)

FOREIGN PATENT DOCUMENTS

WO   WO-2007113727 A2 *  10/2007  ............. G01N 21/31
WO   WO-2012025840 A2 *   3/2012  ......... G01N 33/2823
WO   WO 2013/089764 A1    6/2013

OTHER PUBLICATIONS

International Search Report and the Written Opinion of the International Searching Authority, or the Declaration, dated Mar. 4, 2014, PCT/US2013/057852, 13 pages, ISA/US.

*Primary Examiner* — David P Porta
*Assistant Examiner* — Jeremy S Valentiner
(74) *Attorney, Agent, or Firm* — Haynes and Boone, LLP

(57) ABSTRACT

A downhole system in which an agile light source is used to simulate an integrated optical element to measure one or more characteristics of a fluid in a wellbore.

20 Claims, 8 Drawing Sheets

(51) Int. Cl.
  *G01N 21/31*      (2006.01)
  *G01N 21/33*      (2006.01)
  *G01N 21/3577*    (2014.01)
  *G01N 33/00*      (2006.01)
  *G01N 33/24*      (2006.01)

(52) U.S. Cl.
  CPC ....... *G01N 21/3577* (2013.01); *G01N 33/004* (2013.01); *G01N 33/241* (2013.01); *G01N 33/246* (2013.01); *G01N 33/2823* (2013.01); *G01N 2201/125* (2013.01)

(56) References Cited

U.S. PATENT DOCUMENTS

| | | | |
|---|---|---|---|
| 7,096,053 B2 | 8/2006 | Loeb et al. | |
| 7,760,354 B2 | 7/2010 | Grun et al. | |
| 8,575,541 B1 * | 11/2013 | Jamison | G01N 21/85 250/253 |
| 8,872,100 B1 * | 10/2014 | Perkins | G01N 21/31 250/238 |
| 9,495,505 B2 * | 11/2016 | Perkins | G06F 17/5068 |
| 9,683,932 B2 * | 6/2017 | Pelletier | G01N 21/31 |
| 2005/0213092 A1 | 9/2005 | Mackinnon et al. | |
| 2006/0142955 A1 * | 6/2006 | Jones | E21B 47/102 702/32 |
| 2009/0268203 A1 * | 10/2009 | Uzunbajakava | G01J 3/02 356/436 |
| 2010/0068714 A1 * | 3/2010 | Van Herpen | G01J 3/02 435/6.11 |
| 2010/0302539 A1 * | 12/2010 | Myrick | G01J 3/02 356/326 |
| 2010/0312401 A1 | 12/2010 | Gutierrez et al. | |
| 2011/0108721 A1 | 5/2011 | Ford et al. | |
| 2012/0206725 A1 | 8/2012 | Vukovic-Cvijin et al. | |
| 2012/0211650 A1 * | 8/2012 | Jones | E21B 47/102 250/269.1 |
| 2012/0243880 A1 | 9/2012 | Oda et al. | |
| 2013/0031964 A1 | 2/2013 | Tunheim et al. | |
| 2015/0247755 A1 * | 9/2015 | Pelletier | G01N 21/59 356/440 |
| 2018/0195955 A1 * | 7/2018 | Dai | E21B 47/102 |

* cited by examiner

SIMULATED INTEGRATED COMPUTATIONAL ELEMENTS AND THEIR APPLICATIONS

The present application is a U.S. National Stage patent application of International Patent Application No. PCT/US2013/057852, filed on Sep. 3, 2013, the benefit of which is claimed and the disclosure of which is incorporated herein by reference in its entirety.

BACKGROUND

1. Technical Field

Embodiments disclosed herein relate to the field of optical devices for spectroscopic measurements of a fluid. In particular, embodiments disclosed herein relate to agile light sources for spectroscopic measurements of fluids.

2. Description of Related Art

In the field of oil exploration and extraction there is often the need to perform measurements of samples to determine their chemical composition. In many cases, methods and systems to perform optical measurements use a light source to provide an input light to the sample. Methods and systems to perform optical measurements include filters and other spectrally resolved optical devices that are typically complicated to manufacture, involving time-consuming procedures. State-of-the-art optical measurement techniques are difficult to apply in hydrocarbon exploration and extraction due to the wide spectral range involved in the measurement, covering from the ultra-violet (UV, 250 nm-450 nm), the visible (VIS, 450 nm-750 nm) and near infrared (NIR, 750 nm-2500 nm) to the mid-infrared and beyond (2500 nm-10 μm). Some prior art approaches attempt to overcome the broad band problem by having a plurality of manufactured filters and spectrally resolved optical devices mounted onto a rotating wheel. This approach has the drawback of increasing device overhead in a limited space environment such as the downhole environment, in an oil exploration and extraction application. Furthermore, with filter rotation and fluid flow in an optical cell (e.g., for fluid samples), the measurement system becomes difficult to align and prone to errors. Prior art devices are mechanically and electronically complex systems due to the need for wheel synchronization and mechanical robustness introduced by the rotating filter wheel mechanism. Prior art devices have another drawback in that input light passes through the filters at different times. This adds complexity to data analysis, especially when flow is inhomogeneous, compromising accuracy of results due to undesirable latency caused by the slow rotation of typical filter wheels, and rotation jitter.

Another drawback of conventional filters and other spectrally resolved optical devices is manufacturability. Indeed, filters with spectral profiles may be highly costly to fabricate within a desirable error tolerance. Typically, a desired model is provided to a manufacturer for thin film deposition. During deposition, a real time optimization re-adjusts thicknesses of remaining film layers when a film thickness deviates from a desired value. After filters and spectrally resolved optical devices are manufactured, a calibration process is typically needed to characterize the response of the optical measurement system for samples at different temperatures and pressures. Thus, manufacturing steps in state of the art optical measurement systems introduce error and high cost to the system.

What is needed are methods and systems to allow spectral measurements of samples using a broad spectral band with a reduced number of physical components. Also needed are systems that are rugged and compact, providing detailed information about sample composition, and methods for using the systems.

BRIEF DESCRIPTION OF THE DRAWINGS

Wherever possible, the same reference numbers are used throughout the drawings to refer to the same or like elements.

DETAILED DESCRIPTION

Embodiments disclosed herein provide a rugged and compact optical measurement system that simulates a traditional integrated computational element (ICE) using an alternative integrated computational element (ALICE). As used herein, "ICE" will be used to refer to a traditional or conventional integrated computational element, while "ALICE" will be used to refer to a system that simulates an ICE. To provide detailed compositional information of a sample, some embodiments may use the ALICE to simulate a plurality of ICEs covering an entire optical spectrum of interest, including the UV, VIS, NIR, and MIR spectral regions. Accordingly, in some embodiments a single optical element simulates the plurality of ICEs used in an optical measurement. Thus, embodiments as disclosed herein significantly reduce the complexity of the system, simplifying alignment of different optical components, and boosting reliability of the sensor's mechanical, electrical and electronic components by reducing the number of moving parts.

In some embodiments, a programmable agile light source functions as the ALICE and is the optical element used to simulate a plurality of traditional ICEs by utilizing one or more profiles of the traditional ICEs in conjunction with a spectrally tunable light emitter. A programmable agile light source provides an input light to a sample, the input light having a desired spectral profile by electronic control of the light source power and spectral emission. For example, by scanning an optical signal having a bandwidth across a spectral band and modulating the amplitude of the optical signal utilizing the agile light source, a first ICE may be simulated in an optical system during a first period of time, $\tau_1$. Moreover, by synchronizing a detector in the optical system with the agile light source, a precise measurement using the ALICE system may be completed during or after period $\tau_1$. Likewise, the agile light source may simulate a second ICE during a second period of time $\tau_2$, the detector synchronized for a precise measurement for the second simulated ICE during or after period $\tau_2$. As used herein, agile light source refers to a system including spectrally tunable light sources. One example of a spectrally tunable light source is a wavelength-agile, or equivalently thereto frequency-agile laser, in which the light source provides a spectrally narrowband radiation, and various wavelengths or wavelength ranges of the partial radiation are settable in a rapid and controllable manner.

Figure 1:
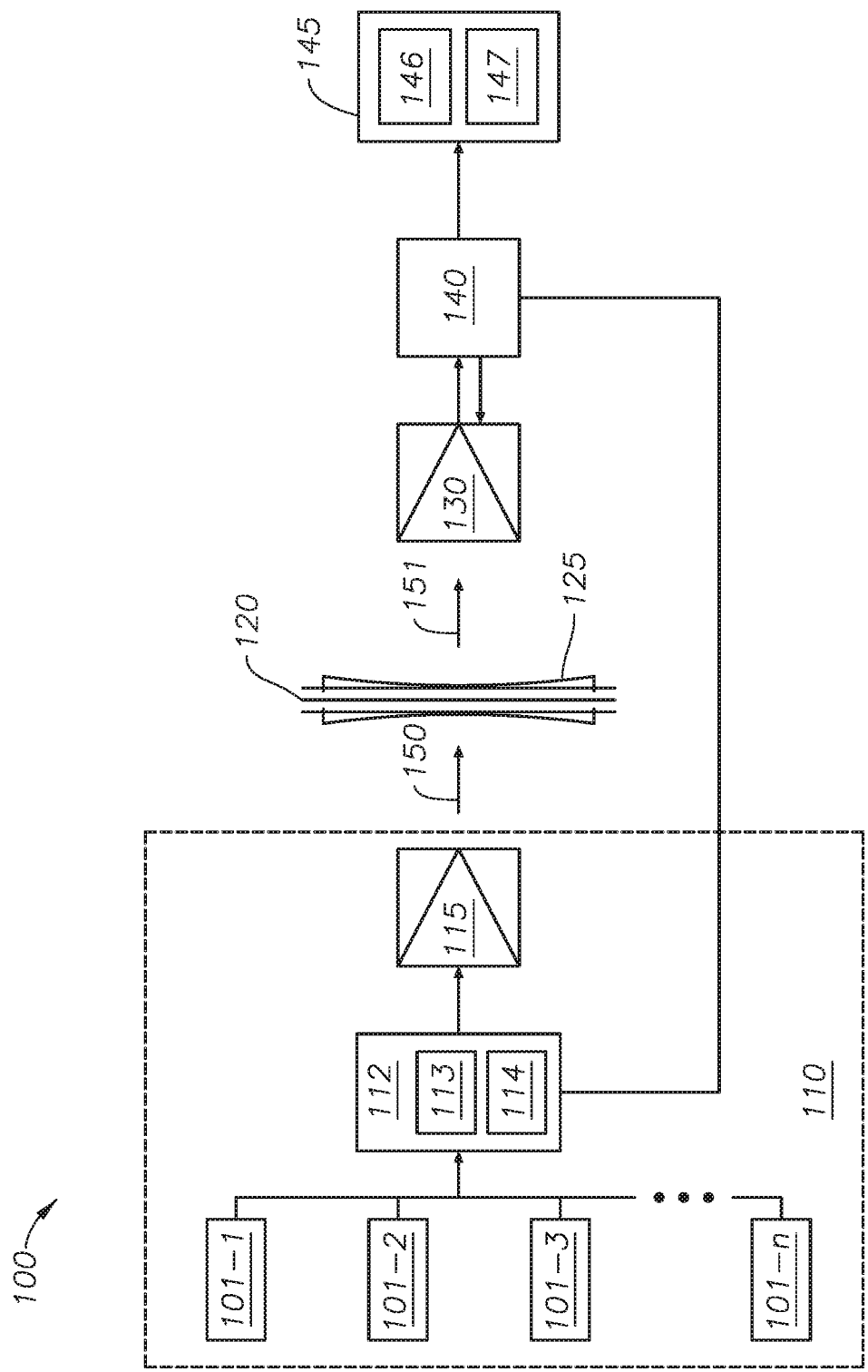
FIG. 1 shows a system to perform an optical measurement of a sample, according to some embodiments.

FIG. 1 shows a system 100 to perform an optical measurement of a sample, according to some embodiments. System 100 includes an agile light source 110, a sample containment area 125 having a sample 120 disposed therein, a detector 130, a controller circuit 140, and an analysis unit 145. Sample containment area 125 may be a cavity, an open or closed container, or simply a window adjacent a sample to be analyzed, such as for example, a window within a conduit or tubular member in which a sample is contained. Light source 110 provides an input light 150 to sample 120. After interacting with sample 120, a sample light 151 is collected and measured by detector 130. Detector 130 converts sample light 151 into an electronic signal and transmits the signal to detector controller circuit 140. Detector controller circuit 140 synchronizes the electronic signal provided by detector 130 with light source 110. The synchronized signal is transmitted to analysis unit 145. Analysis unit 145 includes a processor circuit 146 and a memory circuit 147. Memory circuit 147 stores commands executed by processor circuit 146 to process the synchronized signal provided by controller circuit 140. Memory circuit 147 also stores data collected by analysis unit 145. For example, memory circuit 147 may store a copy of the synchronized signal provided by controller circuit 140.

In some embodiments, sample 120 may be a fluid flowing in a direction, with certain speed. In such configurations, sample area 125 may have an input opening and an output opening, allowing fluid flow through a cavity. In some embodiments, sample 120 may be a static fluid. Further according to some embodiments sample 120 may include a liquid, a solid, a powder, a mud, a colloidal suspension, an oil, a gas, a hydrocarbon, or any combination of the above. Sample 120 may further include a plurality of analytes of interest for an optical measurement. For each of the plurality of analytes in sample 120, an ICE for an analyte may be simulated using an ALICE so that detector 130 determines the analyte composition in sample 120 when input light 150 is modulated to simulate the ICE for an analyte.

Light source 110 may include an emitter 115 providing input light 150, and a source controller circuit 112. As mentioned above, emitter 115 is a spectrally tunable light source such as a wavelength-agile, or equivalently thereto frequency-agile, laser. Source controller circuit 112 may provide electronic signals to emitter 115 so that input light 150 has an amplitude, a bandwidth, and a wavelength. Accordingly, source controller circuit 112 may determine the amplitude, bandwidth and wavelength of input light 150 so that in a selected period of time input light scans a spectral profile corresponding to one of a plurality of conventional ICEs 101-1, 101-2, 101-3, . . . , 101-$n$ (hereinafter collectively referred to as ICEs 101). In that regard, source controller circuit 112 may include a memory circuit 114 to store conventional ICE profiles 101, and a processor circuit 113 to provide the control signal for emitter 115, and to provide a synchronization signal to detector controller 140. Processor circuit 113 performs operations upon executing commands stored in memory circuit 114. One of ordinary skill in the art will recognize that 'n' may be any integer value, such as 3, 4, 10, 20, or even more. In fact, memory circuit 114 may store hundreds or thousands of conventional ICE profiles 101, depending on the desirable use of light source 110. Accordingly, in some embodiments, source controller 112 replaces the physical conventional ICEs and the filter wheel used in the prior art with desired spectral patterns. Processor circuit 113 and memory circuit 114 may include a microprocessor, a field-programmable gate array (FPGA) or an Application-specific Integrated Circuit (ASIC).

Figure 2:
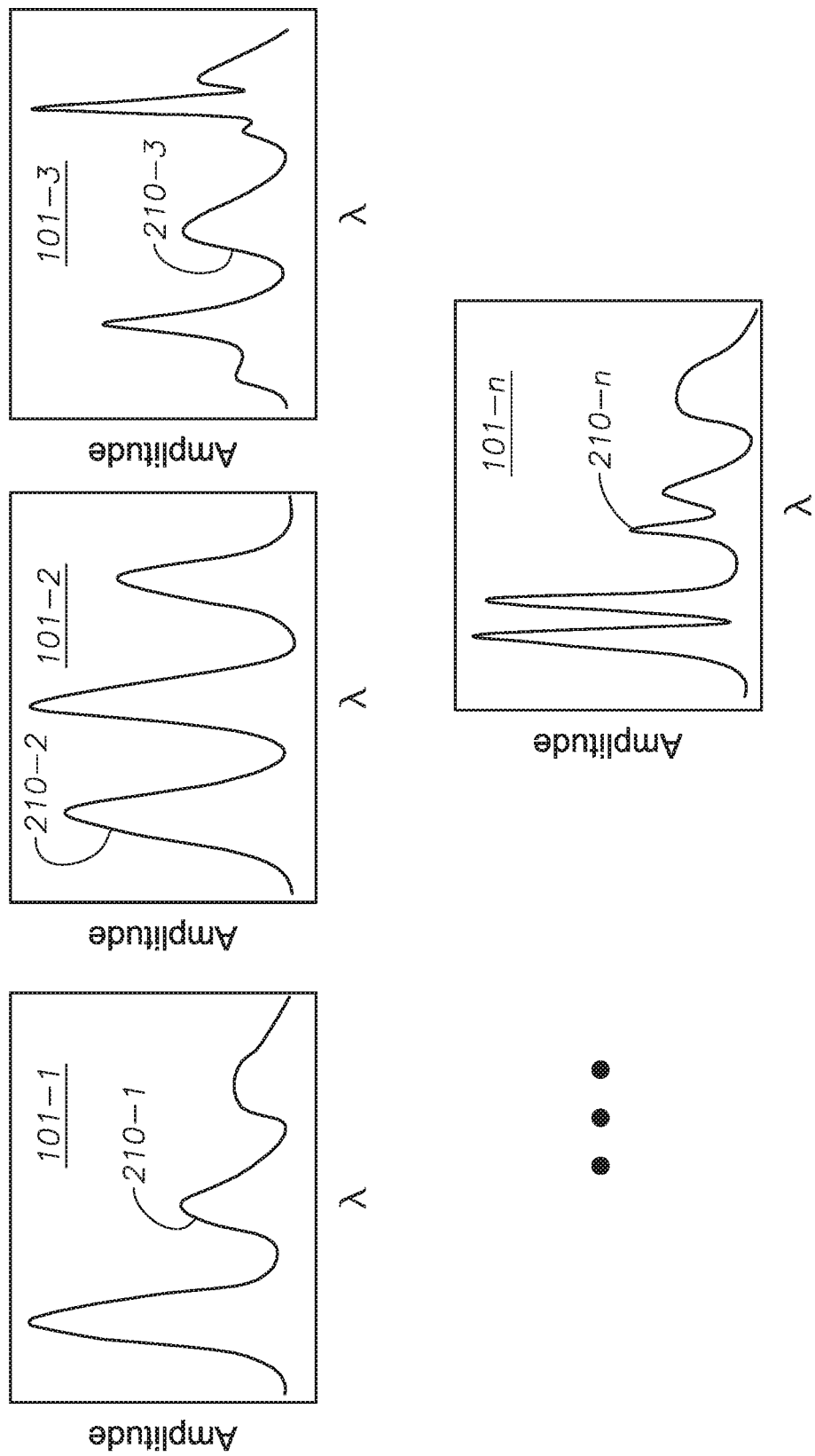
FIG. 2 shows integrated computational element output simulated according to some embodiments.

FIG. 2 shows conventional ICE profiles 101 according to some embodiments. In some embodiments, each one of the ICE profiles 101 may target an analyte whose concentration is desirably measured by system 100. Profiles corresponding to conventional ICEs 101 may be provided to source controller 112 as a list of amplitude values, each amplitude value associated to a center wavelength of operation of light source 115. FIG. 2 illustrates lists of values as curves in a graph, the abscissa of the graph being a wavelength and the ordinate of the graph being an amplitude. For example, curve 210-1 represents ICE profile 101-1, curve 210-2 represents ICE profile 101-2, curve 210-3 represents ICE profile 101-3, and curve 210-$n$ represents ICE profile 101-$n$. Curves 210-1, 210-2, 210-3 and 210-$n$ will be collectively referred hereinafter as ICE curves 210.

ICE curves 210 are selected such that sample light 151 for ICE profile 101-$n$ when collected by detector 130 produces an electric signal related to a measurable characteristic of sample 120. For example, the measurable characteristic of sample 120 may be an analyte concentration in the sample. Other examples of measurable characteristics of a sample may be an octane rating of a gasoline sample. A measurable characteristic of a sample may be a component concentration in a powder; or a grain size in a powder. In some embodiments a measurable characteristic of a sample may be a Gas-Oil ratio (GOR) in a crude oil sample. Crude oil is a liquid containing a mixture of hydrocarbons forming oil, and dissolved gases such as methane $CH_4$, carbon dioxide, $CO_2$, and others. Hydrocarbons of interest in embodiments consistent with the present disclosure may be any one of the group including a $C_1$ hydrocarbon molecule (e.g., methane), a $C_2$ hydrocarbon molecule (e.g., ethanol), a $C_3$ hydrocarbon molecule (e.g., propane), a $C_4$ hydrocarbon molecule, a $C_5$ hydrocarbon molecule, and a $C_6$ hydrocarbon molecule (e.g., a hexane). The dissolved gases will form a gaseous phase at atmospheric conditions. Thus, when crude oil is released into the atmosphere it contains two main phases, a liquid phase which is the commonly known 'oil,' and a gas phase containing natural gas, including methane and other gases. Accordingly, the GOR of a downhole crude oil sample may indicate the value and potential use of a prospective reservoir. Other samples may comprise solids, liquids, gases or a combination of any of the foregoing, formed of one or more substances mixed together.

In some embodiments, it is desirable that the electric signal from detector 130 be linearly correlated to the measurable characteristic of sample 120. In some embodiments, the electric signal may be related to the measurable characteristic by a functional relation including nonlinear terms. The relation between the signal collected by detector 130 for a simulated ICE 101 and the measurable characteristic related to the simulated ICE 101 may be stored in memory circuit 147, in analysis unit 145.

Figure 3:
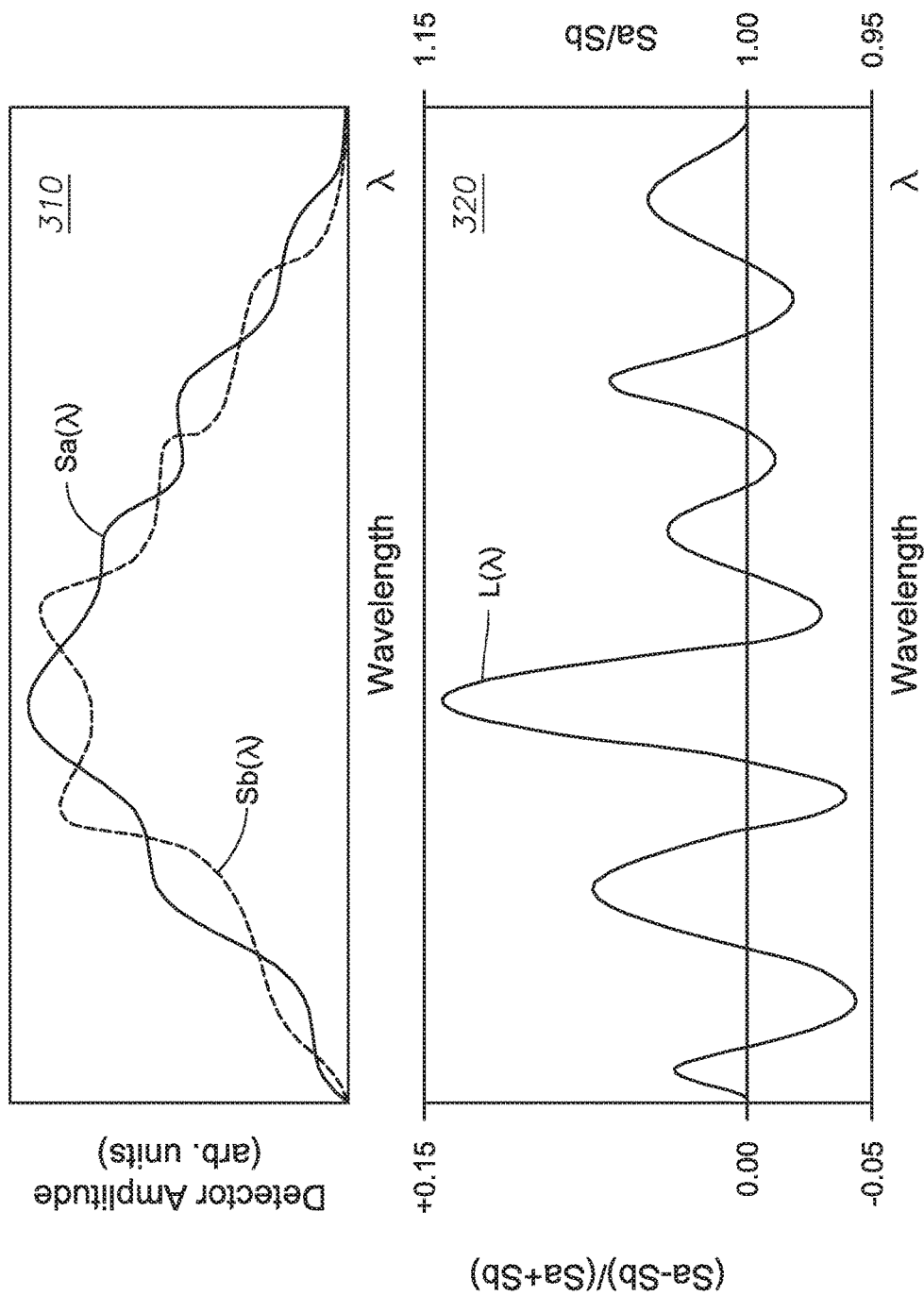
FIG. 3 shows an integrated computational element output and a regression vector according to some embodiments.

FIG. 3 shows a simulated ICE 310 and a regression vector 320 according to some embodiments. In some embodiments, simulated ICE 310 includes two spectral profiles, Sa($\lambda$) and Sb($\lambda$). The two spectral profiles Sa and Sb are defined according to a regression vector 320 ($L_i(\lambda)$, or $L_i$). Regression vector $L_i(\lambda)$ is such that a spectrum $A(\lambda)$ (or A, in vector notation) of sample light 151 resulting from illuminating the sample with input light 150 satisfies the following relation:

$$\kappa_i = \beta \cdot \sum_\lambda A(\lambda) \cdot L_i(\lambda) + \gamma \quad (1)$$

Equation (1) is a linear multivariate problem targeting a measurable property $\kappa_i$, of sample 120. For example, in some embodiments $\kappa_i$ may be the concentration of an analyte of interest in sample 120. In some embodiments, $\kappa_i$ may be an octane rating in a gasoline sample, or a GOR in a crude oil sample. In Eq. (1), $\beta$ is a proportionality constant and $\gamma$ is a calibration offset. Values of $\beta$ and $\gamma$ depend on design parameters of device 100 and not on sample 120. Eq. (1) shows a linear relation between the product $A \cdot L_i$ and measurable property $\kappa_i$. The 'dot' product of vectors A and Li includes a summation over the product of each wavelength component of vectors A and L (cf. summation in Eq. (1)). One of ordinary skill will recognize that a more general functional relation including non-linear terms in the product $A \cdot L_i$ may be used, according to embodiments consistent with the present disclosure.

In some embodiments, spectral curves $S_a$ and $S_b$ in FIG. 3 may be selected such that:

$$L_i(\lambda) = \mu_i \frac{Sa(\lambda) - Sb(\lambda)}{Sa(\lambda) + Sb(\lambda)} + \nu_i \quad (2)$$

Where $\mu_1$ and $\nu_1$ are constants independent of wavelength, suitably chosen to satisfy Eqs. (1) and (2) for measurable property $\kappa_i$, of sample 120.

In some embodiments, spectral curves $S_a$ and $S_b$ in FIG. 3 may be selected such that:

$$L_i(\lambda) = \frac{\delta_{ai} Sa(\lambda)}{\delta_{bi}(Sb(\lambda) + Sa(\lambda))} \quad (3)$$

Where $\delta_{ai}$ and $\delta_{bi}$, are constants independent of wavelength, suitably chosen to satisfy Eq. (1) for measurable property $\kappa_i$, of sample 120.

Figure 4:
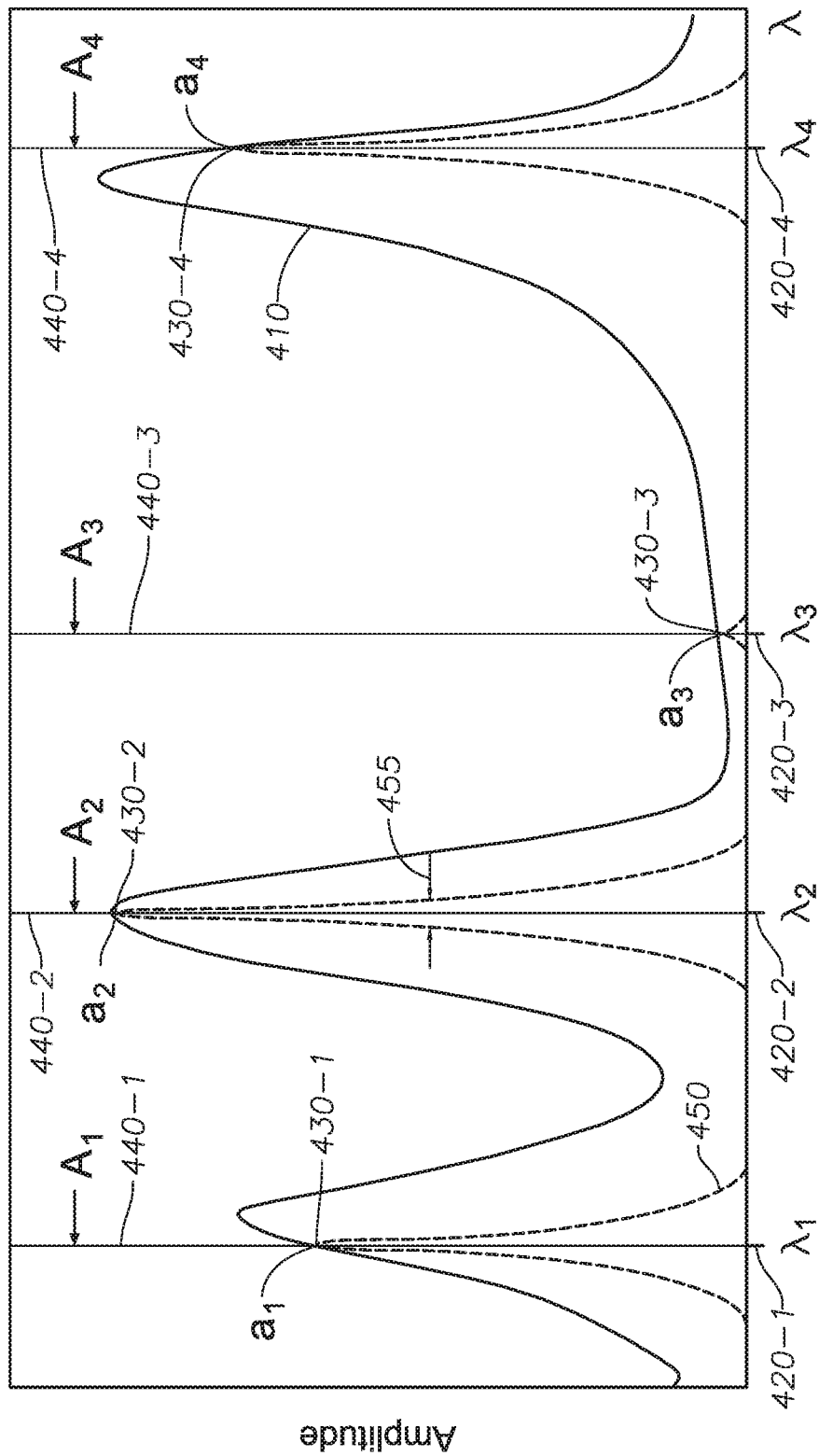
FIG. 4 shows an agile light source forming an integrated computational element, according to some embodiments.

FIG. 4 illustrates an ICE simulation 410 using an agile light source 110 such as is shown in FIG. 1. Agile light source 110 or ALICE is capable of producing an input light 150 having an amplitude 'a' with a given spectral output 450. Spectral output 450 includes a bandwidth 455 centered at a wavelength 420-1 ($\lambda_1$), 420-2 ($\lambda_2$), or 420-3 ($\lambda_3$, collectively referred hereinafter as center wavelength 420). For example, an agile light source may be as provided by Optronic Laboratories of Orlando, Fla. (e.g., Model No. OL 490). In some embodiments a bandwidth 455 of about 6.1 nm may be provided by agile light source 110. Spectral output 450 includes a maximum amplitude $a_1$ 430-1 at wavelength 420-1, a maximum amplitude $a_2$ 430-2 at wavelength 420-2, a maximum amplitude $a_3$ 430-3 at wavelength 420-3, and a maximum amplitude $a_4$ 430-4 at wavelength 420-4. Amplitudes $a_1$, $a_2$, $a_3$, and $a_4$ are collectively referred hereinafter as amplitudes 430. Amplitudes 430 of agile light source 110 match ICE simulation 410 amplitudes 440-1 ($A_1$), 440-2 ($A_2$), 440-3 ($A_3$), and 440-4 ($A_4$, collectively referred hereinafter as ICE amplitudes 440).

Center wavelength 420 may be scanned across a broad wavelength band covering totally or partially the UV, VIS, NIR, and even the MIR spectral regions. By sweeping center wavelength 420 of spectral output 450 through the desired wavelength band, and modulating amplitude 430 at predetermined levels, any desired conventional ICE, such as ICE simulation 410 may be simulated. In that regard, the scanning of center wavelength 420 across the wavelength range of ICE simulation 410 may take a period of time, $\tau$. In such configurations, the signal provided by detector 130 (cf. FIG. 1) may be stored and integrated (or summed over) for the period of time, $\tau$. For example, the signal may be stored in memory 147 and integrated by processor circuit 146. The time integration period may be synchronized with the scanning period of time $\tau$ in source controller 112 by detector controller 140 (cf. FIG. 1).

In some embodiments, ICE simulation 410 may include two spectral curves, $S_a$ collected during time period $\tau_a$, and $S_b$ collected during time period $\tau_b$, as discussed in detail above in relation to FIG. 3. In such configuration, memory circuit 147 may store a signal $A_a$ produced in detector 130 by sample light 151 upon illumination by source light 150 having a spectrum $S_a$. Memory circuit 147 may also store signal $A_b$ produced in detector 130 by sample light 151 upon illumination by source light 150 having a spectrum $S_b$. Processor circuit 146 in analysis unit 145 may integrate a difference or a ratio between signals $A_a$ and $A_b$ over periods of time $\tau_a$ and $\tau_b$. For example, when a linear regression vector $L_i$ is obtained using Eq. (2), processor circuit 146 may integrate the signal from detector 130 as follows:

$$d_i = \mu_i \sum_\lambda \frac{(Aa(\lambda) - Ab(\lambda))}{(Aa(\lambda) + Ab(\lambda))} + \nu_i \quad (4)$$

Likewise, when a linear regression vector Li is obtained using Eq. (3), processor circuit 146 may integrate the signal from detector 130 as follows:

$$d_i = \frac{\delta a_i}{\delta b_i} \sum_\lambda \frac{Aa(\lambda)}{(Aa(\lambda) + Ab(\lambda))} \quad (5)$$

Accordingly, analysis unit 145 may obtain a value for measurement property $\kappa_i$ using Eq. (1) and the value $d_i$ from either Eq. (4) or Eq. (5), as follows:

$$\kappa_i = \beta \cdot d_i + \gamma \quad (6)$$

While the summation (or integral) in Eqs. (4) and (5) is performed relative to wavelength, it is understood that each value $A_a(\lambda)$ and $A_b(\lambda)$ is collected at a specific time, which may be different for $A_a$ and for $A_b$. For example, a value $A_a(\lambda_j)$ may be collected at a time $\tau_{ai}$ within interval $\tau_a$, and a value $A_b(\lambda_j)$ may be collected at a different time $\tau_{bj}$ within interval $\tau_b$. Accordingly, time intervals $\tau_a$, and $\tau_b$ may be overlapping or non-overlapping. Furthermore, in some embodiments a portion of time interval $\tau_a$ may occur between two portions of time interval $\tau_b$. For example, in some embodiments the wavelength scan of agile light source forming ICE 310a and ICE 310b (cf. FIG. 3) may alternate sequentially between an amplitude value for $S_a$ and an amplitude value for $S_b$ for every wavelength, $\lambda$.

Figure 5:
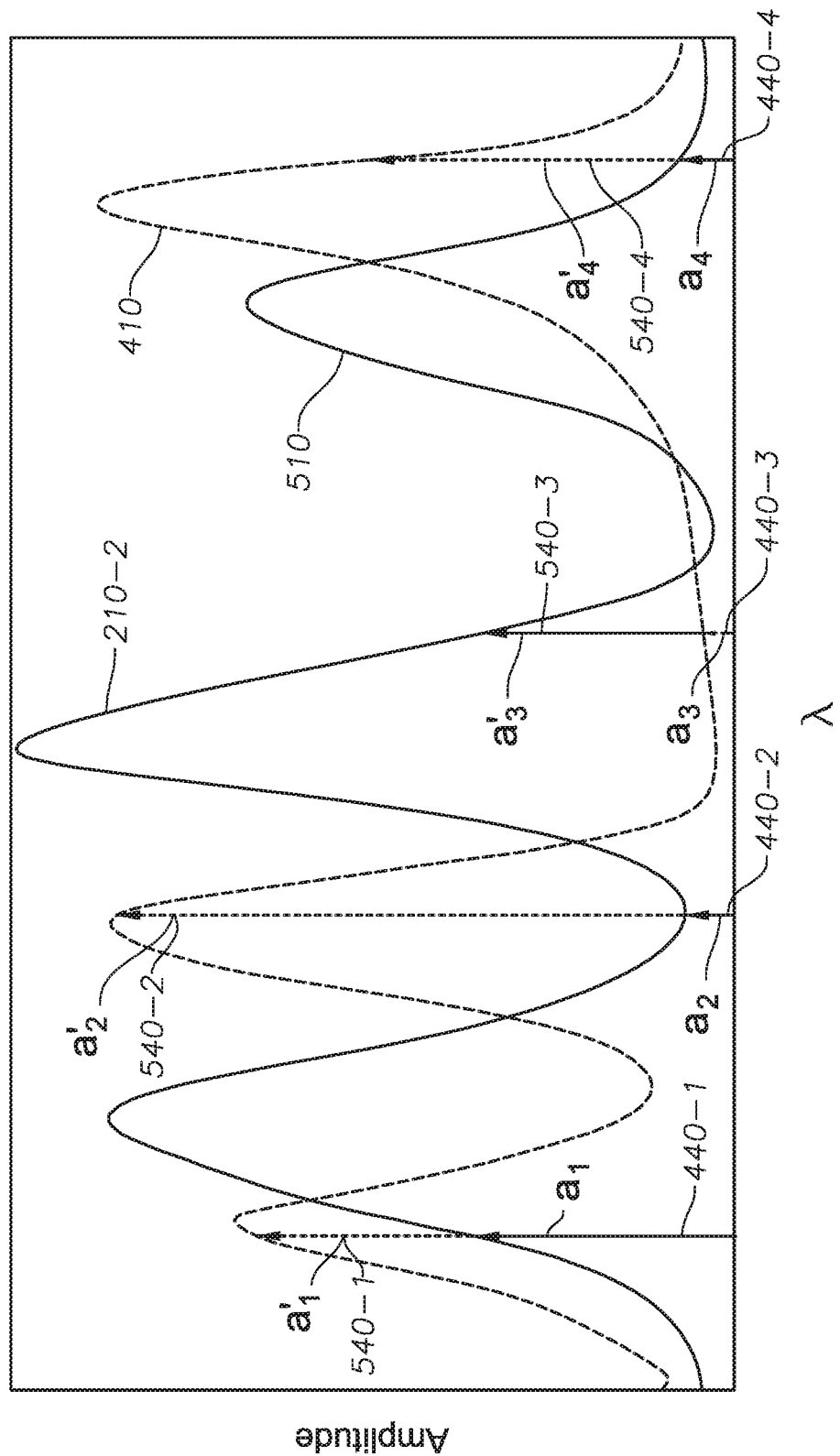
FIG. 5 shows an agile light source forming two integrated computational elements, according to some embodiments.

FIG. 5 illustrates the use of an agile light source or ALICE to simulate multiple conventional ICEs, resulting in ICE simulation 410 and ICE simulation 510, according to some embodiments. In some embodiments, ICE simulation 410 may be selected for a measurement property $\kappa_i$, and ICE simulation 510 may be selected for a different measurement property $\kappa_j$. Further according to some embodiments, ICE simulation 410 may be related to an $S_a$ component of an ICE model, and ICE simulation 510 may be related to an $S_b$ component of the same ICE model, as described in detail above in relation to Eqs. (1-3) and FIG. 3. In that regard, an optical measurement system as system 100 may be configured to measure a plurality of different measurement components, and for each component a regression vector $L_i$ may be defined by two ICE curves $S_a$ and $S_b$ as ICE simulation 410 and ICE simulation 510 in FIG. 5. ICE simulation 410 is as described in detail above (cf. FIG. 4). ICE simulation 510 includes input light amplitude 540-1 ($a'_1$), 540-2 ($a'_2$), 540-3 ($a'_3$), and 540-4 ($a'_4$, hereinafter collectively referred to as light amplitudes 540).

Thus, for example, agile light source 110 may provide a source light amplitude 440-1 forming ICE simulation 410 at a first time, and a source light amplitude 540-1 forming ICE simulation 510 at a second time. While source light amplitude 440-1 may be different from source light amplitude 540-1, and the times at which the amplitudes are provided to sample 120 may also be different, the center wavelength of the source light may be the same for amplitudes 440-1 and 540-1. Source controller 112 stores in memory circuit 114 the times at which signal amplitudes 440 and 540 are provided, and the corresponding wavelengths. Thus, detection controller 140 is able to correlate an amplitude of input light 150 for each signal generated in detector 130 by sample light 151, whether coming from ICE simulation 410 or from ICE simulation 510. This information may be used by analysis unit 145 to perform the signal integration and other operations shown in Eqs. (4-6) above, ultimately providing values for a plurality of measurement properties $\kappa_i$.

With reference back to FIG. 1 and ongoing reference to FIG. 5, a plurality of spectral patterns or ICE profiles 101 corresponding to an ICE simulation, such as ICE simulation 410 as shown in FIG. 5, may be stored in the memory circuit 114 of source controller circuit 112 prior to a measurement. In some embodiments, ICE profiles 101 may be stored in real-time into source controller circuit 112. Moreover, in some embodiments source controller circuit 112 may be configured to adjust one or more of ICE profiles 101 on-the-fly, that is, during a measurement. For example, while performing a measurement with optical system 100, a reference measurement may be collected using a sample having a known measurable property. When the reference measurement shows an error, processor circuit 113 may modify the ICE profile 101 associated to the measurable property, apply it to the sample measurement in real-time, and store it in memory circuit 114.

Alternatively, one or more ICE profiles 101 can be downloaded into memory circuit 114 during sampling operation. For example, when a new property is requested for measurement, an ICE profile 101 associated to the new property may be downloaded into memory circuit 114 via wireless communication, or over a wired network. Once the new ICE profile 101 is stored in memory 114, processor circuit 113 may apply it in real-time to emitter circuit 115. The operational flexibility of optical measurement system 100 allows the optimization of fluid analysis on the fly, to best suit changing fluid or sampling conditions.

Accordingly, light source 110 may be adapted for tool calibration. A known or recently analyzed fluid spectrum can be recast to expected conditions of an upcoming measurement to calibrate at a finer scale the response under field conditions. For example, an ICE profile 101 may be slightly modified by processor circuit 113 according to a model that accounts for different sample temperatures, pressures, or different gas, liquid or solid concentrations based on input from a sensor 116. Sensor 116 may be, for example, disposed to measure a condition of the local environment, such as temperature or pressure. The model and commands for applying the model may be stored in memory circuit 114. Accordingly, embodiments of light source 110 as disclosed herein may be adaptable and recalibrated without performing complex calibration steps which are required for manufacturing conventional multi-layer ICEs. In some embodiments, the ICE profiles 101 corresponding to traditional ICEs are digitally stored as part of agile light source 110 (e.g., in memory circuit 114), so that the ICE profile 101 in use by light source 110 may be altered or modified or changed without taking optical measurement system 100 out of a measurement setting. Such configurations accrue significant cost reduction since only a single agile light source is necessary to satisfy needs from different field operations. In that regard, some embodiments eliminate the need to design and manufacture traditional ICEs for different analytes in different fields. Cost reduction is also accrued through reduction in mechanical, electrical and electronic complexity of the sensor package due to the elimination of a rotating wheel. This leads to increase in tool robustness and lower maintenance cost due to a simpler mechanical and electrical design. Thus, by incorporating a plurality of ICE profiles 101 as part of the system, the ALICE or agile lite source 110, provides significant flexibility to be quickly adjusted in situ.

Figure 6:
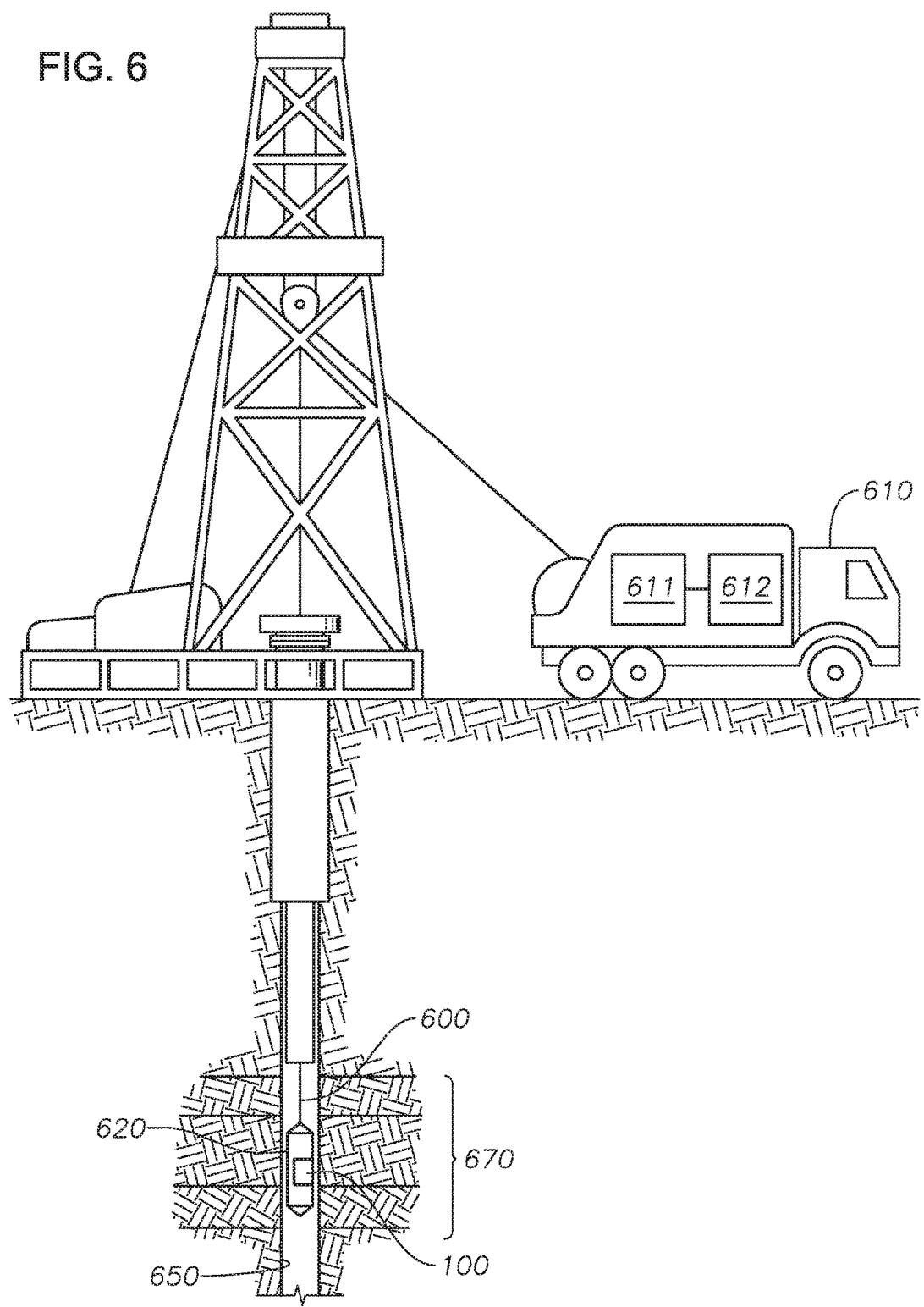
FIG. 6 shows a system to perform an optical measurement of a sample in a wireline logging application, according to some embodiments.

FIG. 6 shows a system to perform an optical measurement of a sample in a wireline logging application, according to some embodiments. Wireline logging includes measurements of fluids and substrates in wellbores drilled for oil and hydrocarbon exploration. In some embodiments, a surface unit 610 includes a processor circuit 611 and a memory circuit 612 to provide commands for sensor 620 to perform measurements and store data obtained from the measurements. Accordingly, once a wellbore 650 has been drilled, a wireline logging measurement may be performed by introducing sensor 620 into wellbore 650, using a wireline 600. Wellbore 650 may traverse through a layered ground formation 670. Sensor 620 may have an optical measurement system 100 including an agile light source, as disclosed herein (cf. FIG. 1). Furthermore, sensor 620 may include a portion of an optical delivery system to deliver input light 150 and a portion of an optical collection system to collect sample light 151 (cf. FIG. 1). In some embodiments, a portion of the light delivery system, agile light source 110, and source controller circuit 112 may be included in surface unit 610. Likewise, a portion of the optical collection system may be included in surface unit 610, such as detector 130, detector controller circuit 140, including an analog-to-digital converter. In some embodiments, the optical delivery system and the optical collection system may include an optical fiber, or fiber bundle. The optical fiber or fiber bundle carries input light 150 and sample light 151 along wireline 600.

Figure 7:
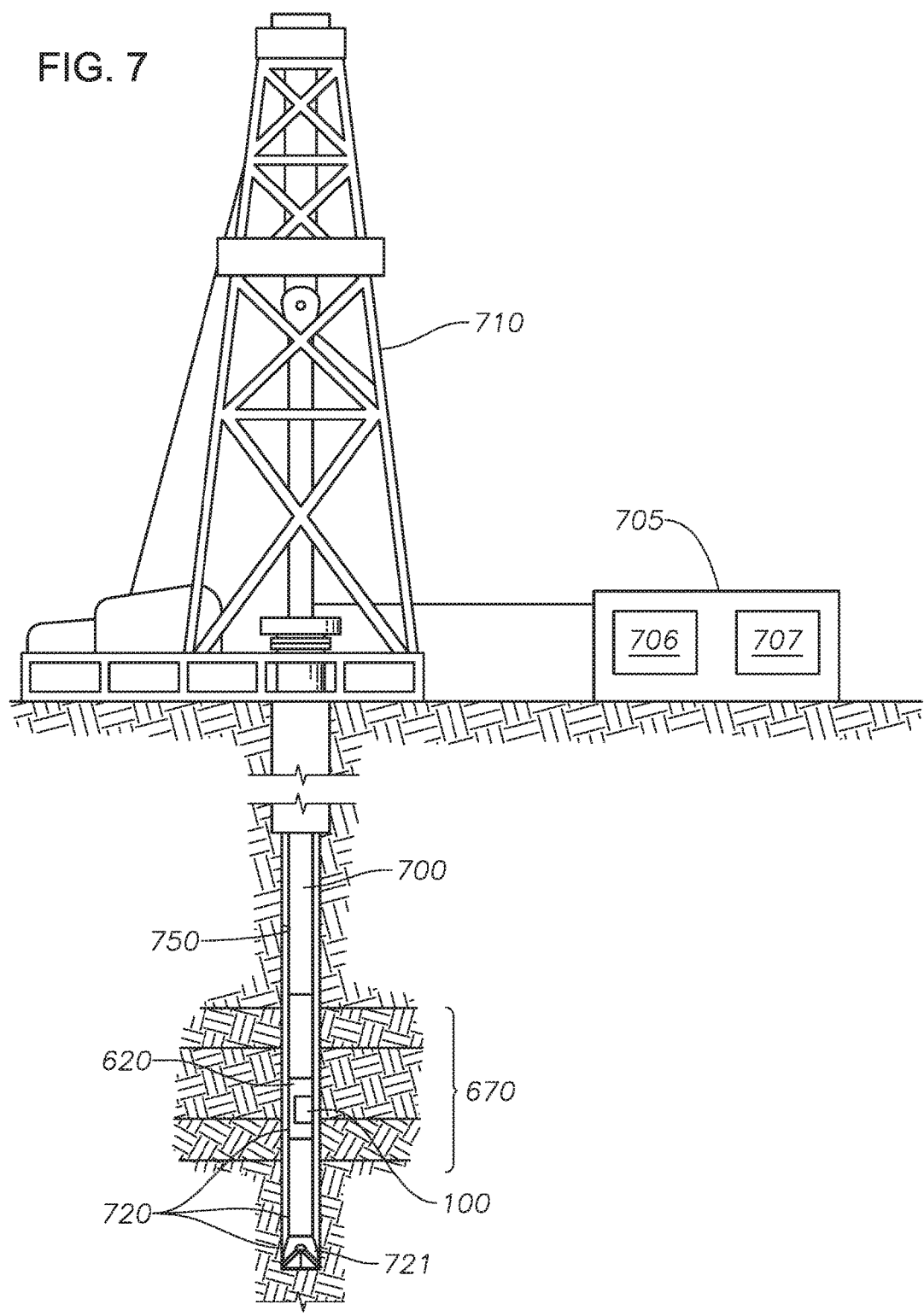
FIG. 7 shows a drill bore including a sensor in a system to perform an optical measurement in a sample for a logging-while-drilling (LWD) application, according to some embodiments.

FIG. 7 illustrates the deployment of an optical measurement system 100 during wellbore drilling operations, permitting logging-while-drilling (LWD) application of system 100, according to some embodiments. An LWD configuration logs desired measurements, such as acoustic, electromagnetic and optical data while a wellbore is being drilled. According to FIG. 7, a drill string 700 carries a bottomhole assembly 720 which includes a drill bit 721 utilized to drill a wellbore 750, traversing through layered ground formation

670. Drilling operations may be operated by a controller 705. A drilling rig 710 provides structural support to drill string 700. Controller 705 may include a processor circuit 706 and a memory circuit 707. Memory circuit 707 stores commands and data used by processor circuit 706 to control the drilling operations, such as controlling one or more functions of bottomhole assembly 720. Bottomhole assembly 720 includes sensor 620. Sensor 620 includes an optical measurement system 100, as described in detail above (cf. FIGS. 1 and 6). Optical measurement system 100 may include all or a portion of an optical delivery system and all or portion of a light collection system, as described in detail above (cf. FIG. 6). In some embodiments, the optical delivery system and the optical collection system may include an optical fiber, or fiber bundle to carry input light 150 and/or sample light 151. In some embodiments, the optical fiber or fiber bundle may be carried by or otherwise integrated into drill string 700.

In some embodiments, optical measurement system 100 as disclosed herein may be implemented in permanent monitoring applications. For example, in an oil extraction rig similar to drilling rig 710, optical measurement system 100 may determine the chemical composition of the extracted hydrocarbons during regular operations. Further according to some embodiments, optical measurement system 100 may be used in a subsea environment of a wireline operation (cf. FIG. 6), an LWD operation (cf. FIG. 7), or a permanent monitoring operation. In some embodiments, the optical fiber or fiber bundle of system 100 may be carried by or otherwise integrated into risers or other tubular components of the drilling system.

Figure 8:
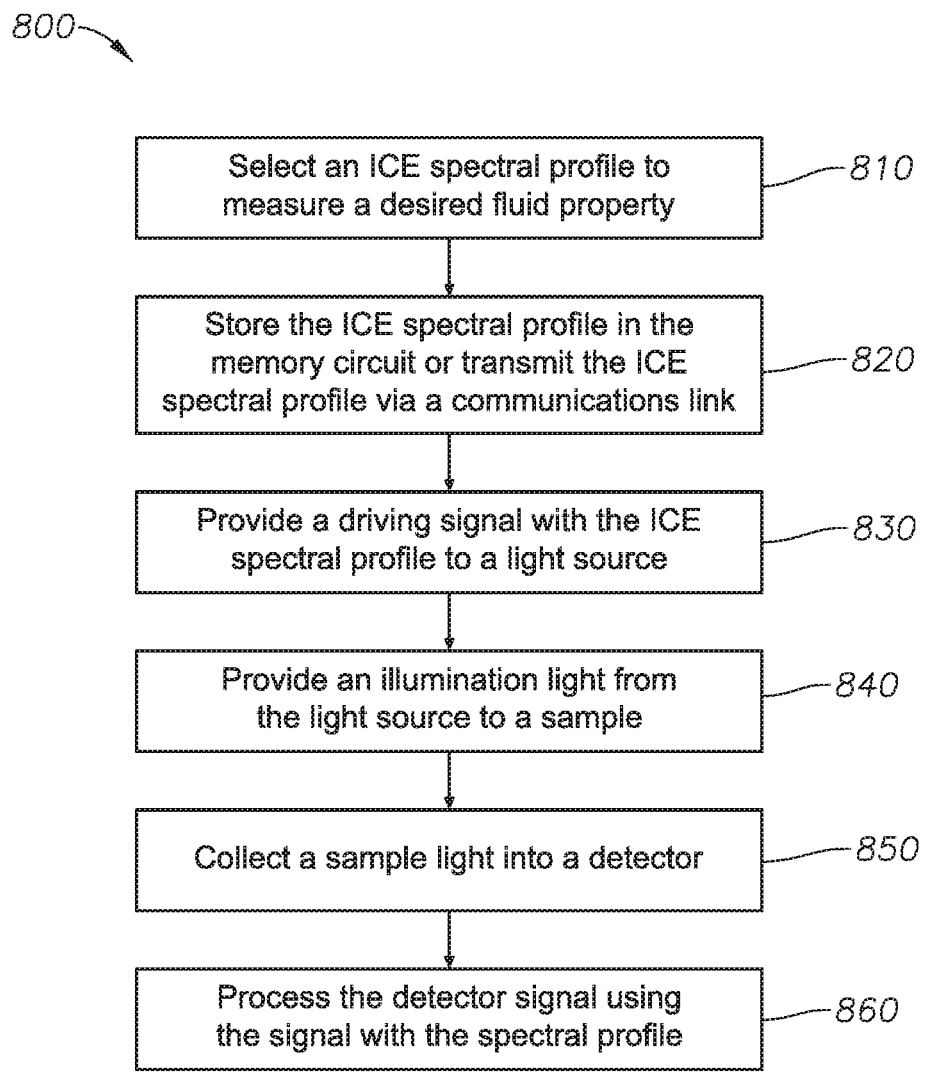
FIG. 8 shows a flowchart in a method to perform an optical measurement of a sample, according to some embodiments.

FIG. 8 shows a flowchart in a method 800 to perform an optical measurement of a sample, according to some embodiments by using an agile light source to simulate one or more integrated optical elements. Steps in method 800 may be performed partially or completely by a processor circuit (e.g., processor circuits 113 or 146, cf. FIG. 1) executing commands stored in a memory circuit (e.g., memory circuits 114 or 147, cf. FIG. 1), in a controller circuit (e.g., source controller circuit 112 or analysis unit 145, cf. FIG. 1). Moreover, some steps in method 800 may be partially or completely performed by an operator controlling a sensor including an optical measurement system (e.g., sensor 620 and optical measurement system 100, cf. FIGS. 6 and 7). Thus, the operator may use a processor circuit executing commands stored in a memory circuit, the processor circuit and the memory circuit being part of a controller circuit (e.g., in a LWD application or a wireline application, cf. FIGS. 6 and 7). The operator may also executing real time commands from a surface controller to produce desired optic responses downhole.

To simulate an ICE as described herein in order to measure a characteristic or property of an analyte, step 810 includes selecting an ICE spectral profile to measure a desired fluid property. Step 820 includes storing the ICE spectral profile in a memory circuit or alternatively, sending the ICE spectral profile via a communication link to a light source. Step 830 includes providing a driving signal with the ICE spectral profile to a light source. Step 840 includes driving a light source with the ICE spectral profile so as to provide an illumination light from the light source to a sample. Step 850 includes collecting a sample light into a detector. Step 860 includes processing the detector signal with the spectral profile of 810. In another embodiment, a second ICE spectral profile, different from the first ICE spectral profile, may be used to drive the light source so as to measure a different characteristic or property of the analyte. It will be appreciated that the driven light may be cycled through a plurality of ICE spectral profiles in a short amount of time, thereby permitting a plurality of measurements to be made quickly. In certain embodiments, the foregoing method may be practiced during drilling of a wellbore as described above or during logging of a wellbore.

In one embodiment, an optical measurement system comprises: a light source to provide an input light, the light source having a source controller circuit; a sample containment area; a detector to detect a sample light; a spectral profile for an integrated computational element; and a detector controller circuit to synchronize the input light and the detector and to implement the spectral profile in order to provide a light signal to simulate an integrated computational element in a period of time with the input light.

In the practice of the foregoing, the optical measurement system may be enhanced by any one of the following, either alone or in combination with one another:

An analysis unit configured to integrate a signal from the detector over the period of time and provide a value of a measurable property of the sample.

A plurality of different spectral profiles for an integrated computational element.

Spectral profiles for a plurality of different integrated computational elements.

The sample containment area comprises one of a cavity, and open or closed container or a window adjacent a sample to be analyzed.

The integrated computational element profile includes a first spectrum and a second spectrum, the first spectrum and the second spectrum selected according to a linear regression vector for a measurable property of the sample. The signal from the detector comprises a difference between a signal from the first spectrum and a signal from the second spectrum, or alternatively, the signal from the detector comprises a ratio of a signal from the first spectrum and a sum of the signal from the first spectrum and a signal from the second spectrum.

A drilling system having a drilling rig, a drill string, a bottomhole assembly carried by the drill string; a drill bit carried by the bottomhole assembly, wherein at least a portion of the optical measurement system is carried by the drill string or forms part of the bottomhole assembly. The system may further include optical fiber carried by drill string connecting portions of the optical measurement system.

A wellbore monitoring system having a wireline, slickline, coiled tubing or cabling deployed in a wellbore and supporting at least a portion of the optical measurement system. The system may further include optical fiber carried by the wireline, slickline, coiled tubing or cabling, connecting portions of the optical measurement system.

In one embodiment, a light source for use in an optical measurement system has a light source comprising: a light emitting circuit having a pre-selected center wavelength, a pre-selected amplitude, and a bandwidth; and a controller circuit to provide a signal to the light emitting circuit to simulate an integrated computational element in a period of time with the input light; wherein the controller circuit comprises a memory circuit, the memory circuit comprising an spectral profile having a first spectrum and a second spectrum associated with the simulated integrated computational element.

In the practice of the foregoing, the light source may be enhanced by any one of the following, either alone or in combination with one another:

The spectral profile comprises a wavelength range greater than the bandwidth of the light emitting circuit; and the signal provided to the light emitting circuit comprises the pre-selected center wavelength and the pre-selected amplitude.

The wavelength range of the light source comprises the pre-selected center wavelength within at least the bandwidth of the light emitting circuit.

The light emitting circuit can provide input light with the pre-selected amplitude for the first spectrum at a first time, and can provide input light with the pre-selected amplitude for the second spectrum at a second time.

The first time is included in a first period of time and the second time is included in a second period of time.

The first period of time overlaps at least a portion of the second period of time.

The first period of time and the second period of time are interleaved so that the second time is subsequent to the first time.

A weighted difference between the first spectrum and the second spectrum is proportional to a regression vector associated to a measurable property of a sample.

A ratio of the first spectrum to a sum of the first spectrum and the second spectrum is proportional to a regression vector associated to a measurable property of a sample.

A plurality of different spectral profiles for an integrated computational element.

Spectral profiles for a plurality of different integrated computational elements.

In one embodiment, a method for measuring a desired property of a sample comprises: selecting an integrated computational element (ICE) spectral profile to measure the desired property; providing a driving signal with the ICE spectral profile to a light source; providing an illumination light from the light source to the sample based on the ICE spectral profile; collecting a sample light in a detector; and processing the detector signal using a collection signal with the spectral profile.

In one embodiment, a method for measuring a desired property of a sample comprises: simulating an integrated computational element using an agile light source; and measuring a property of the sample using the simulated integrated computational element.

In the practice of the foregoing, the methods for measuring a desired property of a sample may be enhanced by any one of the following, either alone or in combination with one another:

Processing the detector signal further comprises synchronizing the collection signal with the driving signal.

Selecting an ICE spectral profile comprises finding a linear regression vector using a first spectral profile and a second spectral profile.

Selecting an ICE spectral profile comprises selecting a plurality of spectral profiles to measure a plurality of desired properties.

Storing a plurality of different spectral profiles for an integrated computational element.

Storing spectral profiles for a plurality of different integrated computational elements.

Selecting a plurality of ICE spectral profiles to measure a plurality of desired properties comprises measuring at least one property of the group consisting of an octane rating, a gas-oil-ratio (GOR), a hydrocarbon composition, a carbon dioxide (CO2) composition, and a water (H2O) composition.

Measuring the hydrocarbon composition comprises measuring any one of the group consisting of a C1 hydrocarbon molecule, a C2 hydrocarbon molecule, a C3 hydrocarbon molecule, a C4 hydrocarbon molecule, a C5 hydrocarbon molecule, and a C6 hydrocarbon molecule.

Providing an illumination light in a wellbore from the light source to a sample in the wellbore, either during wireline, slickline or coiled tubing operations in the wellbore or during drilling of the wellbore Embodiments described herein are exemplary only. One skilled in the art may recognize various alternative embodiments from those specifically disclosed. Those alternative embodiments are also intended to be within the scope of this disclosure. As such, the embodiments are limited only by the following claims.

What is claimed is:

1. An optical measurement system comprising:
a light source to provide an input light, the light source having a source controller circuit;
a sample containment area;
a detector configured to detect a sample light and produce a detector signal;
a spectral profile for an integrated computational element; and
a detector controller circuit configured to synchronize the input light and the detector and configured to implement the spectral profile, wherein the detector controller circuit is configured to provide and adjust in-situ a light signal to simulate the integrated computational element in a period of time with the input light,
wherein the light signal is adjusted in-situ by way of the light source.

2. The optical measurement system of claim 1 further comprising an analysis unit configured to integrate a signal from the detector over the period of time and provide a value of a measurable property of the sample.

3. The optical system of claim 1, wherein the detector signal comprises a difference between a signal from a first spectral curve and a signal from a second spectral curve.

4. The optical system of claim 1, wherein the detector signal comprises a ratio of a signal from a first spectral curve and a sum of the signal from the first spectral curve spectrum and a signal from a second spectral curve.

5. A light source for use in an optical measurement system, the light source comprising:
a light emitting circuit having a pre-selected center wavelength, a pre-selected amplitude, and a bandwidth; and
a controller circuit configured to provide and adjust in-situ a signal to the light emitting circuit to simulate an integrated computational element in a period of time with an input light;
wherein the controller circuit comprises a memory circuit, the memory circuit comprising a spectral profile having a first spectral curve and a second spectral curve associated with the simulated integrated computational element.

6. The light source of claim 5 wherein the spectral profile comprises a wavelength range greater than the bandwidth of the light emitting circuit; and the signal provided to the light emitting circuit comprises the pre-selected center wavelength and the pre-selected amplitude.

7. The light source of claim 6 wherein the wavelength range comprises the pre-selected center wavelength within at least the bandwidth of the light emitting circuit.

8. The light source of claim 5 or 6 wherein the light emitting circuit can provide input light with the pre-selected amplitude for the first spectral curve at a first time, and can provide input light with the pre-selected amplitude for the second spectral curve at a second time.

9. The light source of claim 8 wherein the first time is included in a first period of time and the second time is included in a second period of time.

10. The light source of claim 9 wherein the first period of time overlaps at least a portion of the second period of time.

11. The light source of claim 9 or 10 wherein the first period of time and the second period of time are interleaved so that the second time is subsequent to the first time.

12. The light source of claim 5, wherein a weighted difference between the first spectral curve and the second spectral curve is proportional to a regression vector associated to a measurable property of a sample.

13. The light source of claim 5, wherein a ratio of the first spectral curve to a sum of the first spectral curve and the second spectral curve is proportional to a regression vector associated to a measurable property of a sample.

14. A method for measuring a desired property of a sample, the method comprising:
  selecting at least one an integrated computational element (ICE) spectral profile to measure the desired property;
  providing a driving signal with the ICE spectral profile to a light source, wherein the driving signal and light source are adjustable in-situ;
  providing an illumination light from the light source to the sample based on the ICE spectral profile;
  collecting a sample light in a detector; and
  processing the detector signal using a collection signal with the spectral profile.

15. The method of claim 14 wherein processing the detector signal further comprises synchronizing the collection signal with the driving signal.

16. The method of claim 14 wherein selecting an ICE spectral profile comprises selecting a plurality of spectral profiles to measure a plurality of desired properties.

17. The method of claim 16 further comprising measuring at least one property of the group consisting of an octane rating, a gas-oil-ratio (GOR), a hydrocarbon composition, a carbon dioxide ($CO_2$) composition, and a water ($H_2O$) composition.

18. The method of claim 17 wherein measuring the hydrocarbon composition comprises measuring any one of the group consisting of a $C_1$ hydrocarbon molecule, a $C_2$ hydrocarbon molecule, a $C_3$ hydrocarbon molecule, a $C_4$ hydrocarbon molecule, a $C_5$ hydrocarbon molecule, and a $C_6$ hydrocarbon molecule.

19. An optical measurement system comprising:
  an alternative integrated computational element (ALICE) configured to provide an input light, the ALICE comprising a spectrally tunable light emitter and a spectral profile for an integrated computational element (ICE);
  a sample containment area;
  a detector configured to detect a sample light; and
  a detector controller circuit configured to synchronize the input light and the detector and further configured to implement the spectral profile such that the input light from the ALICE is adjustable in-situ and simulates an integrated computational element=wherein the input light from the ALICE is adjusted in-situ by way of the ALICE.

20. The system of claim 19, wherein the spectrally tunable light emitter is a laser.

* * * * *